United States Patent [19]
Ryan

[11] Patent Number: 5,338,314
[45] Date of Patent: Aug. 16, 1994

[54] ROTATING Y-CONNECTOR

[75] Inventor: William P. Ryan, Plymouth, Minn.

[73] Assignee: B. Braun Medical, Inc., Bethlehem, Pa.

[21] Appl. No.: 869,340

[22] Filed: Apr. 16, 1992

Related U.S. Application Data

[63] Continuation-in-part of Ser. No. 688,176, Apr. 22, 1991, Pat. No. 5,205,831.

[51] Int. Cl.[5] .................................. A61M 25/00
[52] U.S. Cl. .................................. 604/284; 604/167; 604/283
[58] Field of Search ............. 604/283, 284, 167, 274, 604/256

[56] References Cited

U.S. PATENT DOCUMENTS

| | | | |
|---|---|---|---|
| 4,419,094 | 12/1983 | Patel | 604/93 |
| 4,475,548 | 10/1984 | Muto | 604/167 |
| 4,496,348 | 1/1985 | Genese et al. | 604/167 |
| 4,723,550 | 2/1988 | Bales et al. | 604/256 |
| 4,809,679 | 3/1989 | Shimonaka et al. | 604/187 |
| 4,817,637 | 4/1989 | Dormandy, Jr. et al. | 604/283 |
| 4,857,062 | 8/1989 | Russell | 604/167 |
| 4,895,346 | 1/1990 | Steigerwald | 604/167 |
| 4,929,235 | 5/1990 | Merry et al. | 604/167 |
| 4,932,633 | 6/1990 | Johnson et al. | 251/149.1 |
| 4,978,341 | 12/1990 | Niederhauser | 604/167 |
| 5,009,391 | 4/1990 | Steigerwald | 251/149.1 |
| 5,045,061 | 9/1991 | Seifert et al. | 604/283 |
| 5,088,984 | 2/1992 | Fields | 604/284 |
| 5,092,857 | 3/1992 | Fleisehhacker et al. | 604/256 |
| 5,129,887 | 7/1992 | Euteneuer et al. | 604/283 |
| 5,158,553 | 10/1992 | Berry et al. | 604/256 |

FOREIGN PATENT DOCUMENTS 2063679 6/1981 United Kingdom .

Primary Examiner—Paul J. Hirsch
Attorney, Agent, or Firm—Hugh D. Jaeger

[57] ABSTRACT

A Y-connector with a compression gasket for compressing about a guidewire or catheter when inserted into an inner chamber of a Y-connector and compressed by a rim of a large knurled knob. When the large knurled knob is twisted with an inward force, the rim engages the gasket with inward compression, causing the center portion of the gasket to expand inwardly, thereby frictionally engaging against a guidewire or catheter. The inner expansion of the gasket is substantially equal about the inner circumference of the gasket, thereby providing a seal between the guidewire catheter and bodily fluids, such as blood. A guidewire clamp is included at the end of a side arm extending from the Y-connector body.

4 Claims, 16 Drawing Sheets

ROTATING Y-CONNECTOR

CROSS REFERENCES TO CO-PENDING APPLICATIONS

This application is a continuation-in-part of U.S. Ser. No. 07/688,176, filed Apr. 22, 1992, now U.S. Pat. No. 5,205,831 entitled "Compression Gasket for Y-Connector" to the same assignee as the present patent application.

BACKGROUND OF THE INVENTION

1. Field of the Invention

The present invention relates to a medical device, and more particularly, pertains to a Y-connector with a sealing gasket, guidewire clamp and a swivel luer for use in guidewire procedures, catheter procedures, or other related medical procedures.

2. Description of the Prior Art

Prior art Y-connectors have experienced problems of creating or maintaining adequate seals between a guidewire or catheter and the Y-connector, particularly the longitudinal chamber of the Y-connector to which a catheter or guidewire is inserted through. If an adequate seal is not maintained between the guidewire or the catheter, body fluids leak out which is not only impractical, but is also unsanitary.

Prior art gaskets and Y-connectors were usually a piece of tubing, such as silicon tubing, which did not provide a good gasket when compressed between the Y-connector and the guidewire or catheter. This caused not only body fluids to leak out, but also did not provide for easy sliding of the guidewire, and most dangerously, sometimes compressed the catheter so that the catheters were then unusable and had to be replaced. This was certainly impractical since replacement of a catheter would usually result in expenditures of a couple hundred dollars for replacement of the catheter because of the collapsing of the catheter by the ill-fitting or ill-compressed gasket.

Guidewires in prior art were often left unsecured in an unorderly fashion near the Touhy Borst adapter, sometimes allowing for longitudinal movement of a guidewire in the adapter or kinking or bending of the guidewire immediately adjacent to the Touhy Borst adapter.

Often it is desirable to rotate a catheter tube either before cavity insertion or subsequent to insertion where it is advantageous to rotate the catheter tube as it is slid into and further along into a vein, artery or other body member. This usually entails the process of rotating the y-adapter and catheter as a single unit or disconnecting the catheter from the y-adapter to accomplish catheter rotation by itself followed by reconnection of the y-adapter to the catheter.

It is also important to consider the operation of the side ports of the y-adapter with relationship to peripheral components attached thereto.

The present invention overcomes the disadvantages of the prior art by providing a Y-connector with a compression gasket which provides for even compression about a guidewire or catheter, and also provides for sliding of the guidewire or catheter. Also provided is a guidewire clamp for positive positioning of a guidewire with reference to the Y-connector. A swivel luer is also provided between the y-connector body and a catheter for rotational positioning of the y-connector with respect to the catheter.

SUMMARY OF THE INVENTION

The general purpose of the present invention is to provide a Y-connector, compression gasket, a guidewire clamp and with a Touhy Borst adapter for medical procedures, such as in cardiology, particularly angioplasty.

A Y-connector with an hour glass configured compression gasket equalizes compression about a guidewire or catheter so that the guidewire or catheter can be easily slid through the longitudinal opening of the Y-connector, and yet at the same time, block seepage of any body fluids, such as blood, past the compression gasket.

The single and double Touhy Borst Y-connector is for use in angioplasty procedures. The Y-connector allows for easy insertion and sealing about a flimsy medical device, such as an angioplasty catheter or guidewire, and provides for a subsequent fluid seal by turning of a knob located at the proximal end. The distal end includes a rotating swivel connector including a quad ring seal.

According to one embodiment of the present invention, there is provided a Y-connector with a Touhy Borst and including the components; namely, a body Touhy Borst, a rotating connector, an hour glass configured compression gasket, a side port, and a guidewire clamp on a side arm. Each component is made of medical grade polymer materials.

The body is the main structure for the Y-connector, and is an injection molded polycarbonate material with two internal lumens configured in a Y orientation. The straight through part of the Y is used for insertion of a medical device and is connected with a Touhy Borst adapter. The branch of the Y contains a female luer connector that can be used for a number of functions including an additional device, injection of flushing medium such as saline, or injection of contrast medium such as Renographin ®.

A highly elastomeric polymer compression gasket positions in the adapter which can be deformed under longitudinal pressure and which has a small central through hole. The Touhy Borst cap is threaded on the rear of the adapter and used to put axial pressure on the compression gasket deforming it around the inserted medical device, such as a guidewire, thus providing a seal. If no device is present, the hole collapses on itself and seals against loss of any fluids.

The last component is a rotating connector which is used to connect the Y-connector to a mating medical device, such as a guiding catheter in an angiography procedure. The rotating connector contains a set of internal luer threads to allow for locking of the Y-connector onto another standard luer connection. A quad seal with both axial and radial compression provides a seal between the body and the rotating connector. Any other suitable seal could be utilized which provides axial and radial compression. Rotation is desirable so that the orientation of the Y-connector can be changed relative to the mating medical device and operating room environment. This is important in positioning the flushing port relative to the patient.

To accommodate the various requirements of interventional cardiology procedures the Y-connector with Touhy Borst can be configured in different configurations, such as in co-pending patent application Ser. No.

07/470,161, filed on Jan. 25, 1990, entitled "Y-connector", now abandoned, by Brucker, and assigned to the same assignee. The difference between these configurations lies in the number of Touhy Borst connectors available on each device and the availability of a side arm. Multiple Touhy Borst are required for interventional cardiology procedures in which two devices must be inserted and positioned in the vascular system. The side arm adapter is required for those procedures in which the guidewire is not coaxial with the center line of the balloon catheter, but lies along the outside of the device. The use of the side arm allows the guidewire position to be fixed independent of the interventional catheter which has the advantage of exchanging catheters without the use of an exchange wire.

According to one embodiment of the present invention, there is provided a compression gasket for a Y-connector which is uniquely configured so that under compression, the inner circumference compresses equally about a guidewire or catheter. The compression gasket includes a cylindrical-like member with an inner rim at a center portion and an outer circumference with an hour glass type configuration at a center portion. Optional vertical reinforcing members extend about the outer circumference between the top and bottom edge, and along the outer circumference of the hour glass configuration. The compression gasket is configured so that equalized pressure between the bottom and top circumferential edges provide that the inner circumference expands inwardly and substantially equally about a guidewire or catheter.

A guidewire clamp secures at the end of a side arm for securement and fixation by snap engagement of a guidewire to the Y-connector.

According to an alternative embodiment, there is provided a rotating y-connector having a compression gasket and a snap-on style swivel luer for rotation of a catheter tube. The rotating y-connector includes two halves which are a y-body and a swivel luer and catheter which rotatingly attach and seal over and about a cylindrical extension extending from the inboard end of the y-body. An O-ring and a snap ring in the junction of the y-body and the swivel luer seal the y-body and swivel luer to one another. A catheter shaft is affixed to and extends from one end of the swivel luer, and is plumbed to the interior of the swivel luer. Finger grip tabs about the swivel luer allow the swivel luer and catheter shaft to be manually rotated with respect to the y-body.

Significant aspects and features of the present invention include a silicon rubber compression gasket for a Y-connector which can be used in any Y-connector type structure.

Another significant aspect and feature of the present invention is a silicon rubber compression gasket for a Y-connector which equally compresses about a guidewire or catheter, providing that the guidewire or catheter can be easily slid through the compression gasket, while the compression gasket also provides a pressure seal against reverse pressure of body fluids, such as blood, trying to pass out through the longitudinal lumen of the Y-connector.

Another significant aspect and feature of the present invention includes a swivel connector with a quad elastomeric seal which utilizes both radial and axial compression.

Other significant aspects and features of the present invention include a ergonomically designed shaft to fit in one's hand, a larger thumb wheel and a large thru lumen.

A further significant aspect and feature of the present invention is a quad elastomeric seal between the body and the rotating connector.

Another significant aspect and feature of the present invention includes a large lumen up to or greater than 9 French. The swivel and cap are snap on components providing fewer moving components for ease of operation. The snap on cap prevents the cap from separating from the body.

A further significant aspect and feature of the present invention includes a frictionally engaging guidewire clamp at one end of a side arm.

Yet a further significant aspect and feature of the present invention is the use of a swivel luer and catheter tube which can be rotated independently of the y-connector body.

Still a further significant aspect and feature of the present invention is the use of a compression gasket in conjunction with a swivel luer in a y-connector.

Another significant aspect and feature of the present invention is a rotating y-connector.

A further significant aspect and feature of the present invention is a y-connector and coupled swivel luer having a snap ring and an O-ring to ensure integrity.

Yet another significant aspect and feature of the present invention is a y-body having a cylindrical extension extending into a bore in a swivel luer.

A still further significant aspect and feature of the present invention is a rotating y-connector having finger grip tabs for turning of the swivel luer and catheter shaft with respect to the y-body.

Having thus described embodiments of the present invention, it is the principal object hereof to provide a Y-connector with a compression gasket and guidewire clamp for use during guidewire or catheter medical procedures.

One object of the present invention is a polymer gasket with an hour glass configuration for engaging about a guidewire, a catheter or other medical device.

Another object of the present invention is a y-connector with a compression gasket and swivel luer.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
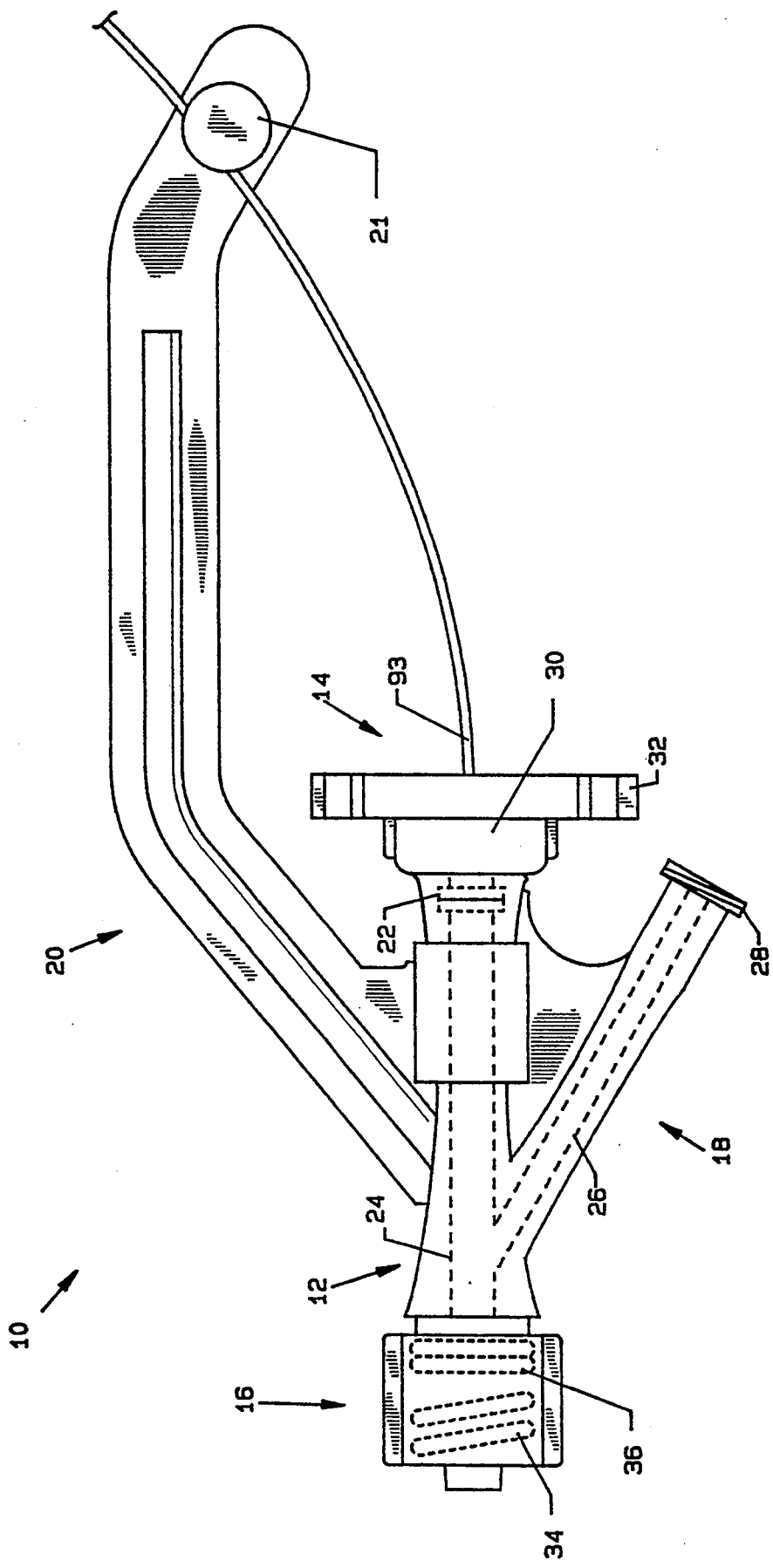
FIG. 1 illustrates a plan view of a Y-connector.

FIG. 1 illustrates a front view of a Y-connector 10, the present invention with major components including a body 12, a Touhy Borst adapter 14, a rotating connector 16, a side port 18, a side arm 20, a guidewire clamp 21, and a compression gasket 22, all of which are described later in detail. Each component is made of medical grade polymer materials. The body 12 is the main structure for the Y-connector 10, and is an injection molded polycarbonate material with two lumens 24 and 26 configured in a Y orientation. The straight through part of the Y containing lumen 24 is used for insertion of a circular medical device and is connected to the Touhy Borst adapter 14. The branch of the Y with the lumen 26 contains a female luer connector 28 that can be used for a number of functions including an additional device, injection of flushing medium such as saline, or injection of contrast medium such as Renographin ®.

One component of the Y-connector 10 is a highly elastomeric compression gasket 22 which can be deformed under pressure and which has a through hole and which rests in a seat. The Touhy Borst cap 30 is threaded and is used to apply pressure longitudinally on the compression gasket 22 deforming it inwardly around the inserted medical device, such as a guidewire, thus providing a seal. If no device is present, the hole collapses on itself and seals against any loss of fluids. The cap 30 includes a large thumb wheel knob 32 for any movement, torquing and locking. The last component is the rotating connector 16 which is used to connect the Y-connector 10 to a mating medical device, such as a guiding catheter. The rotating connector 16 contains a set of internal luer threads 80 to allow for locking of the Y-connector 10 onto another standard luer connection. In addition, rotation is provided about a quad O-ring and/or O-ring 36 as later described in detail in FIG. 3 so that the orientation of the Y-connector 10 can be changed relative to the mating medical device. This is important in positioning the flushing port relative to the patient.

Figure 2:
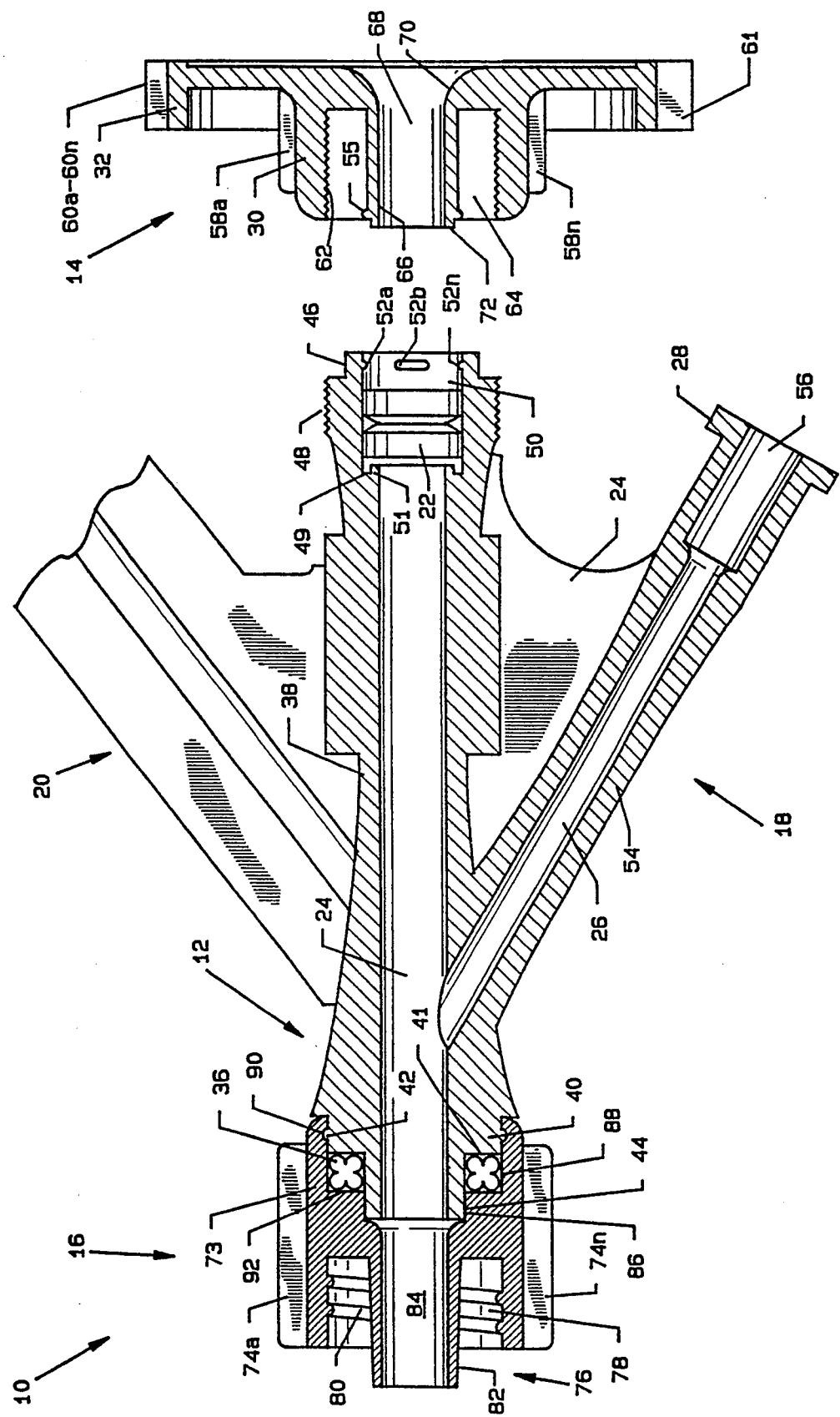
FIG. 2 illustrates a cross-sectional view of the Y-connector with the Touhy Borst cap removed.

FIG. 2 illustrates a cross-sectional view of the Y-connector 10 where all numerals correspond to those elements previously described. Lumen 24 aligns longitudinally along the ergonormally sculptured main body portion 38 of the body 12. A radiused shoulder 40 with an adjoining flat donut like annular surface 41, an annular snap ring 42 and a lesser radiused shoulder 44 extend from the main body 38, and aligns concentrically along the longitudinal center line of the lumen 24 at the left end of the body 12. The quad O-ring and/or O-ring 36 frictionally engages the lesser radiused shoulder 44. A radiused shoulder 46 with adjoining threads 48 extends from the opposing end of the body 12 to align concentrically along the longitudinal center line of the lumen 24. A radiused cavity 50 aligns concentrically with the lesser radiused lumen 24 at the right end of the body 12 and intersects a recessed seat 49. An annular lip 51 extends outwardly to the right from the recessed seat 49 to accommodate and engage the compression gasket 22 as later described in detail. The flexible plastic compression gasket 22 aligns in the radiused cavity 50 in alignment with the recessed seat 49. Protrusions 52a–52n at the mount of the cavity 50 act as keepers to capture the compression gasket 22 in the cavity 50. Lumen 26 aligns within the extension body 54, and intersects and connects with the lumen 24. A cavity 56 aligns with the lumen 26 in conjunction with the female luer connector 28 which aligns concentrically with the lumen 26. Protrusions 52a–52n align at the outer circumference of the cavity 50 to also capture a snap ring 55 on the end of the tubular extension of cap 30 to keep the thumb wheel knob loosely coupled to the body 12.

The Touhy Borst adapter 14 aligns to and threadingly engages the main body 12 and includes a thumb wheel knob 32 and pluralities of gripping ribs 58a–58n and 60a–60n. An index tab or rib 61 is included on the thumb wheel knob 32 of the cap 30. The cap 30 includes internal threads 62 which align and mate with the threads 48 of the body 12. An annular cavity 64 aligns concentrically along the center line of the cap 30 and is bounded by the internal threads 62 and by a concentric tubular extension 66. The tubular extension 66 extends to the left from the thumb wheel knob 32, and includes a passage hole 68 with a flared opening 70. An annular lip 72 extends from the tubular extension 66 to engage and accommodate the compression gasket 22.

The rotating connector 16 includes a round main body 73 with a plurality of external gripping ribs 74a–74n around its outer circumference. A male luer 76 extends longitudinally from the main body 73 through a cavity 78. Raised threads 80 line the cavity 78. The cavity 78, raised threads 80, a ramped cylinder section or male section 82, and surrounding main body 73 form the male luer 76. The passageway 84 formed by the ramped cylinder section 82 aligns concentrically with radiused cavities 86 and 88 and also with a rounded annular groove 90 which is located off-center to the right of the cavity 88. Cavity 88 includes a flat donut like annular surface 92 adjacent to the radiused portion of the cavity 88.

Figure 3:
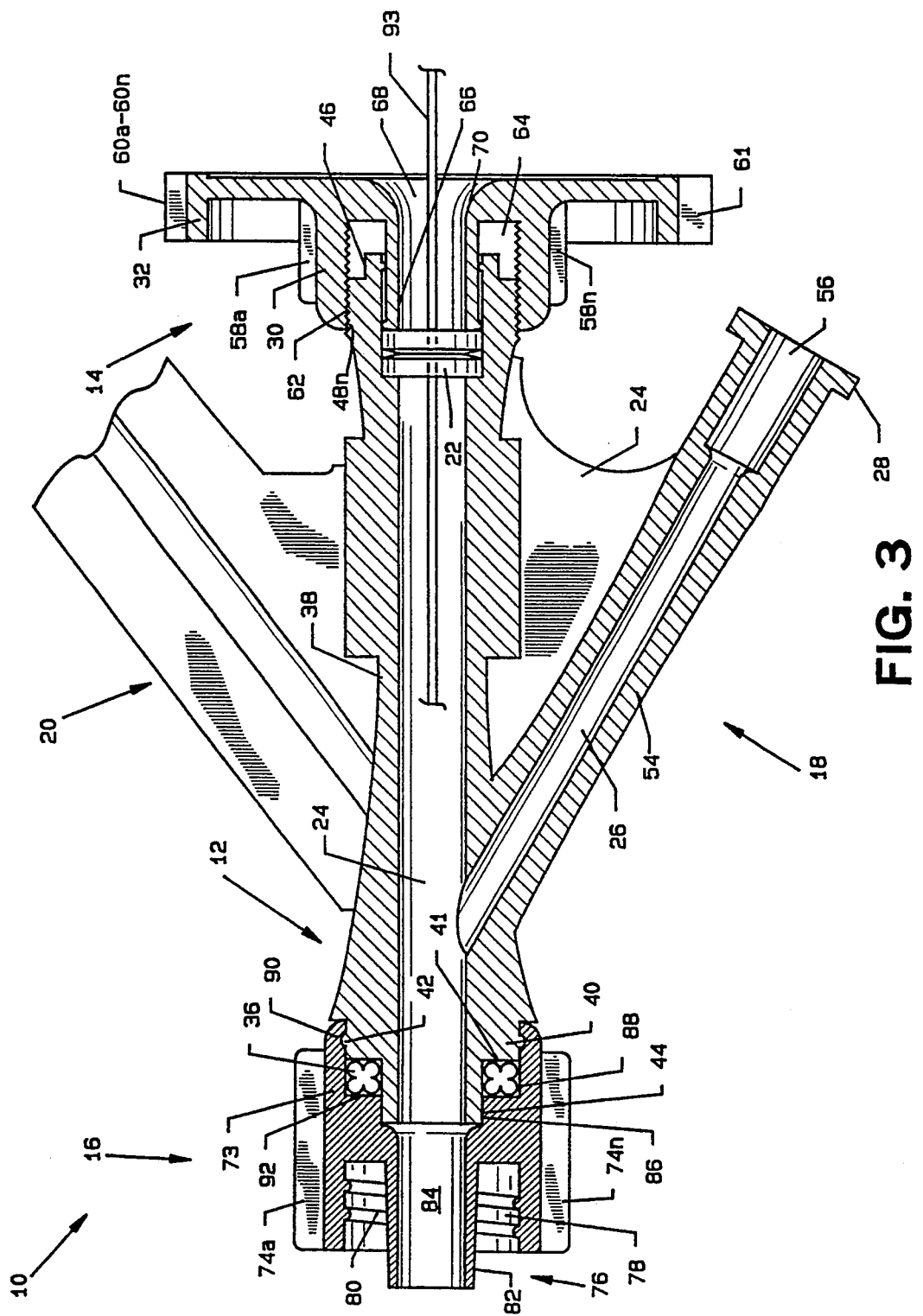
FIG. 3 illustrates a cross-sectional view of a compression gasket for sealing along a guidewire in a Y-connector.

FIG. 3 illustrates an assembled Y-connector 10 where all numerals correspond to those elements previously described. The Touhy Borst adapter 14 is mated to the body 12 by engagement of internal threads 62 and 48. The tubular extension 66 of the Touhy Borst adapter 14 is forced against the compression gasket 22 to cause the effective size of an internal hole in the compression gasket 22 to decrease in diameter to seal against a guidewire 93 as it is pressed against the recessed seat 49 and the annular lip 51 as later described in detail.

The rotating connector 16 snappingly engages the left end of the body 12. The cavity 86 accommodates the radiused shoulder 44 of the body 12. The quad O-ring 36 seals the rotating connector 16 to the body 12 by sealing of its external surfaces against the lesser radiused shoulder 44 of the body 12, the donut like annular surface 41 of the body 12, the circumference of the cavity 88 of the rotating connector 16 and the flat donut like annular surface 92 of the rotating connector 16. The annular snap ring 42 of the body 12 snappingly engages the rounded annular groove 90 of the rotating connector 16 to hold the body 12 and the rotating connector 16 in alignment and to maintain pressure against the quad O-ring and/or O-ring 36.

Figure 4:
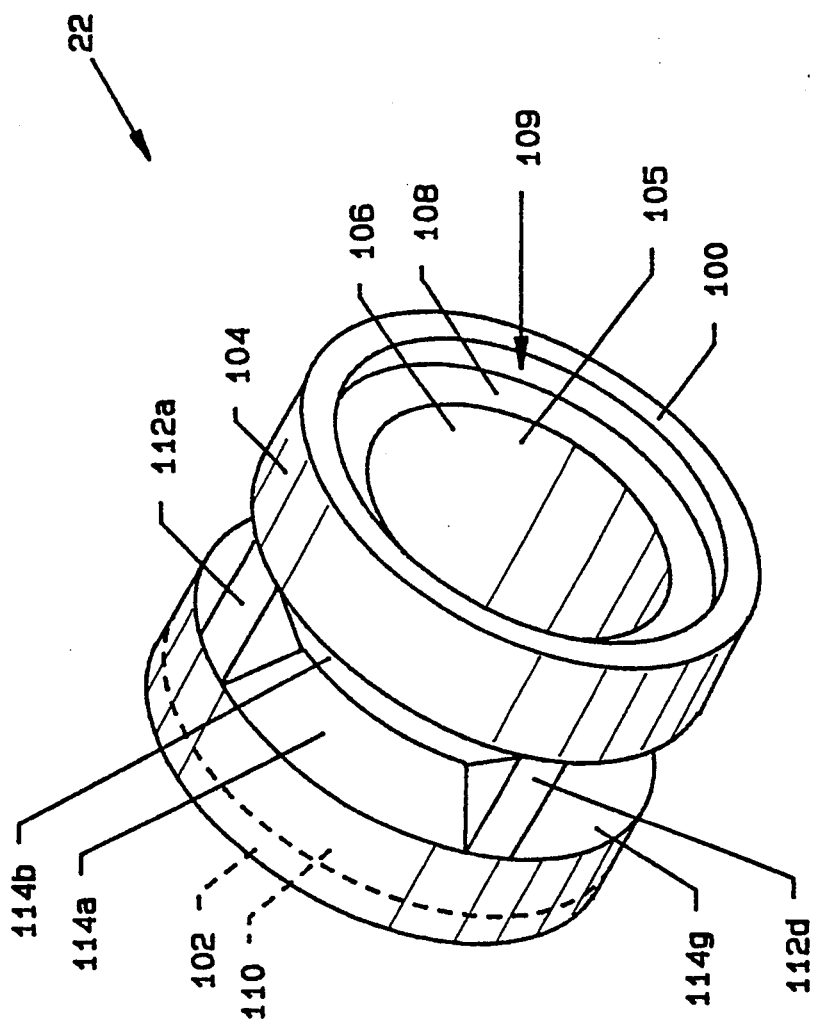
FIG. 4 illustrates a plan view of the compression gasket for a Y-connector, the present invention.

FIG. 4 illustrates a perspective view of the compression gasket 22, which can be made of silicon rubber or any other suitable material, compressible material which has a memory to return to its original geometrical shape when not compressed. Any other suitable materials can be utilized which exhibit compressible qualities and also exhibit memory to return to an original geometrical shape. The compression gasket 22 includes a right edge 100 and a corresponding and opposed left edge 102. The outer circumferential wall 104 is shaped in an hour glass configuration. The particular geometrical configuration of the outer circumferential wall 104 is that as illustrated in the Figure, but it is within the teachings of the present invention to vary the geometrical configuration as to the exact hour glass configuration. An inner hole 105 aligns in the inner circumference 106 and includes an adjacent right annular rim 108, an adjacent a left annular rim 110, each of which is offset with respect to the right edge 100 and the left edge 102. The inner circumference 106 frictionally engages against a guidewire, catheter or medical device as later described in detail. Optional vertical ribs 112a–112d are provided for supporting the right edge 100 with respect to the left edge 102. These vertical ribs cause the compression gasket 22 to internally close in a rhombic configuration about a medical device. Cavity 109 is the space between the right annular ring 108 and the plane of the right edge 100. A similar opposing cavity 111 is the space between the left annular ring 110 and the plane of the left edge 102. Cavities 109 and 111 accommodate the annular lip 72 of the Touhy Borst adapter 14 and the annular lip 51 of the body 12 for compressional alignment of the compression gasket 22 with the lip members 72 and 51, respectively.

Figure 5:
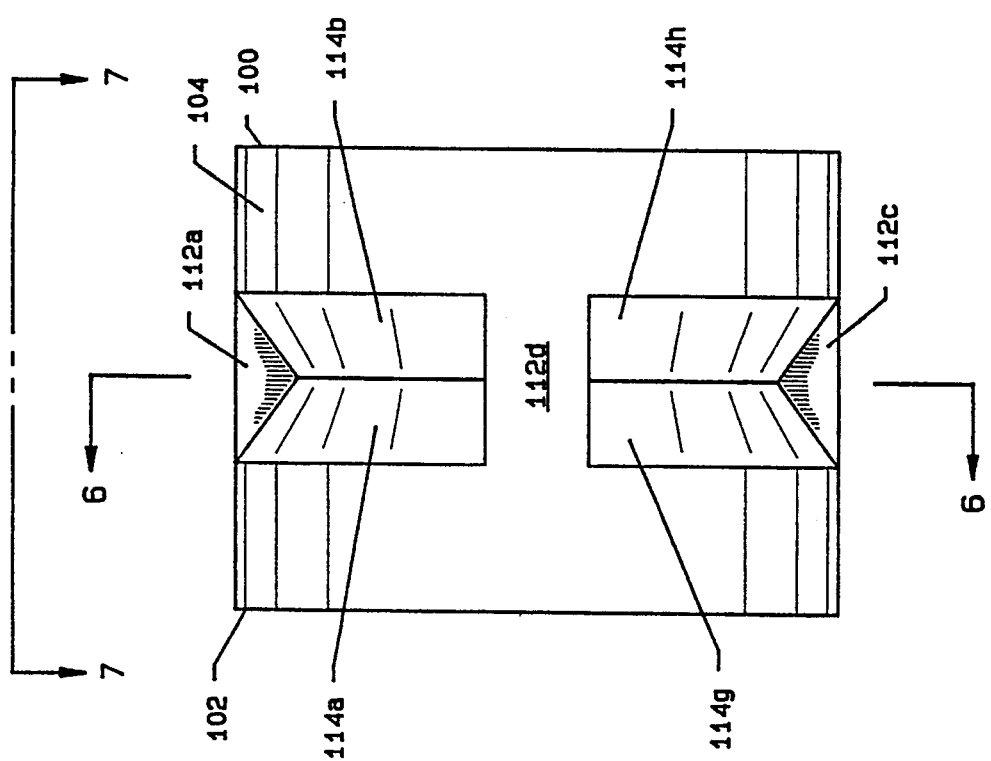
FIG. 5 illustrates a top view of FIG. 4.

FIG. 5 illustrates a side view of FIG. 4 where all numerals correspond to those elements previously described. Angled walls 114a and 16b align between the ribs 112a and 112d and the outer circumferential wall 104 as illustrated. Angled walls 114c–114d, 114e–114f and 114g–114h align between the ribs 112a–112d and about the circumferential wall 104 in a similar fashion.

Figure 6:
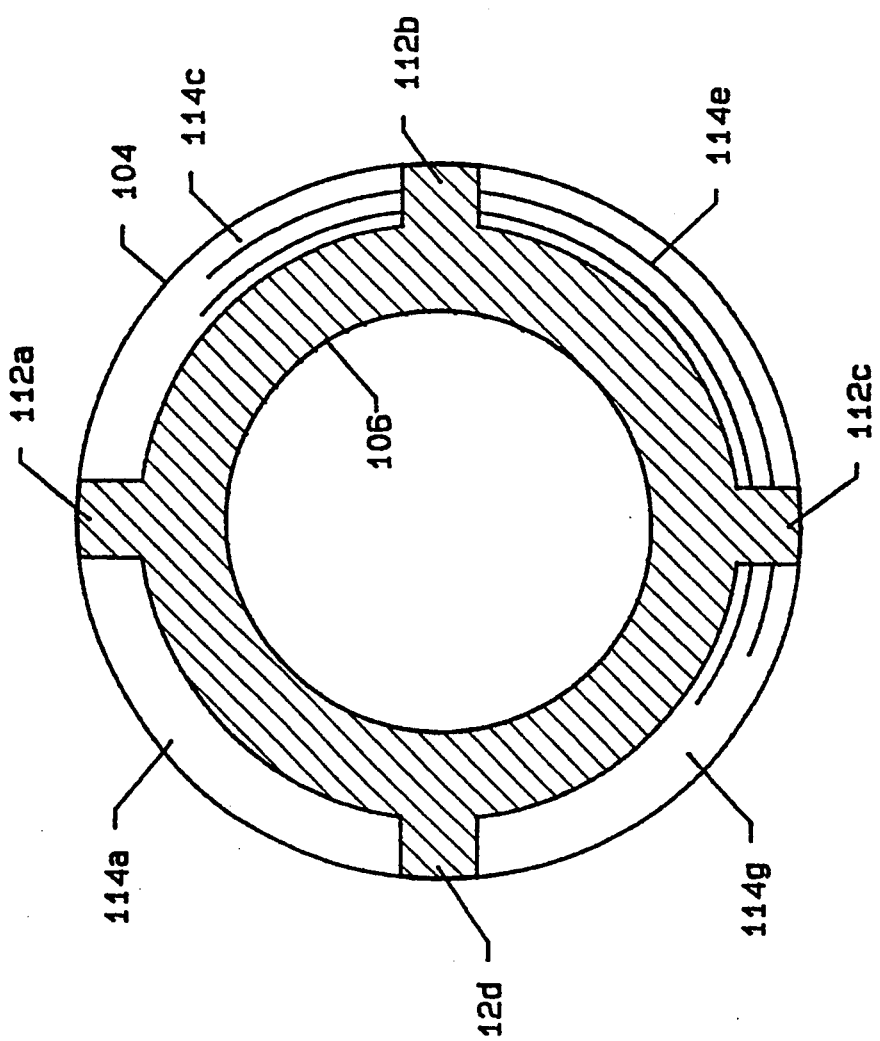
FIG. 6 illustrates a view taken along line 6—6 of FIG. 5.

FIG. 6 illustrates a sectional view taken along line 6—6 of FIG. 5 where all numerals correspond to those elements previously described.

Figure 7:
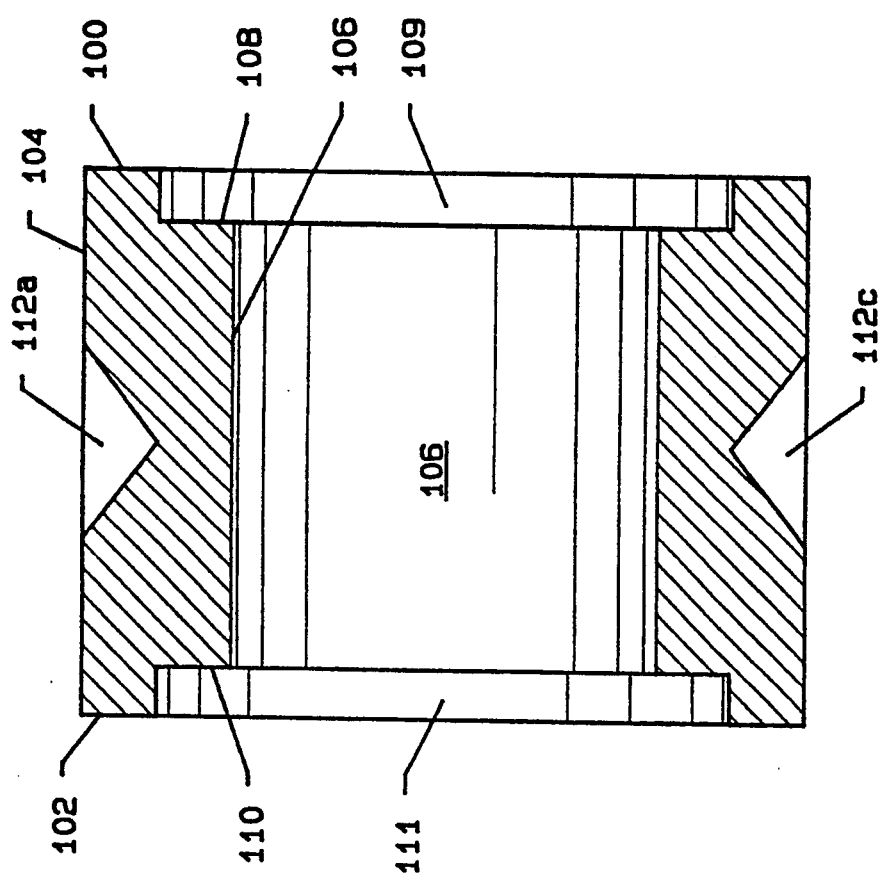
FIG. 7 illustrates a view taken along line 7—7 of FIG. 5.

FIG. 7 illustrates a sectional view along line 7—7 of FIG. 5 where all numerals correspond to those elements previously described.

MODE OF OPERATION

Figure 8:
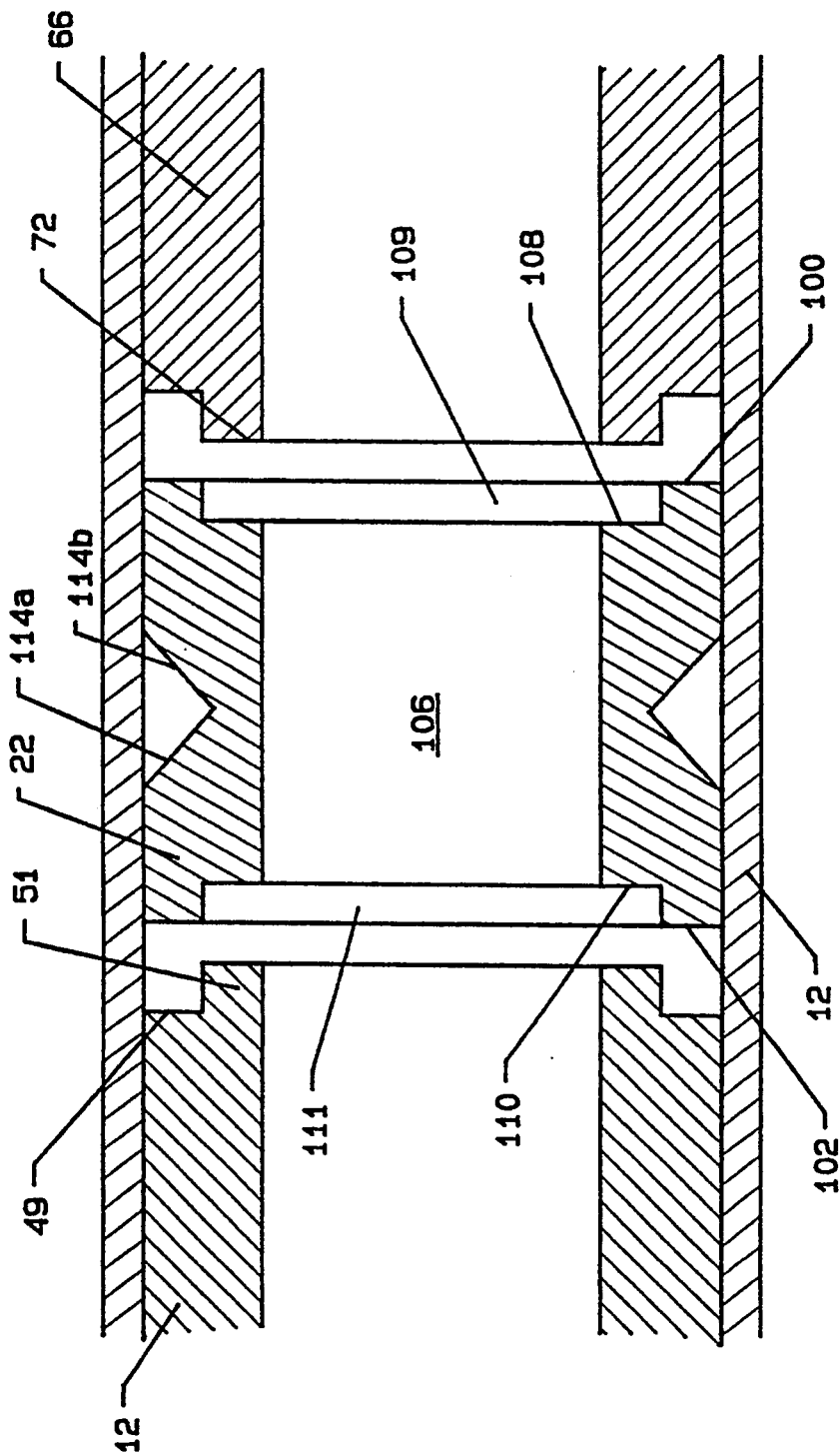
FIG. 8 illustrates alignment of the compression gasket in the body of the Y-connector.
Figure 9:
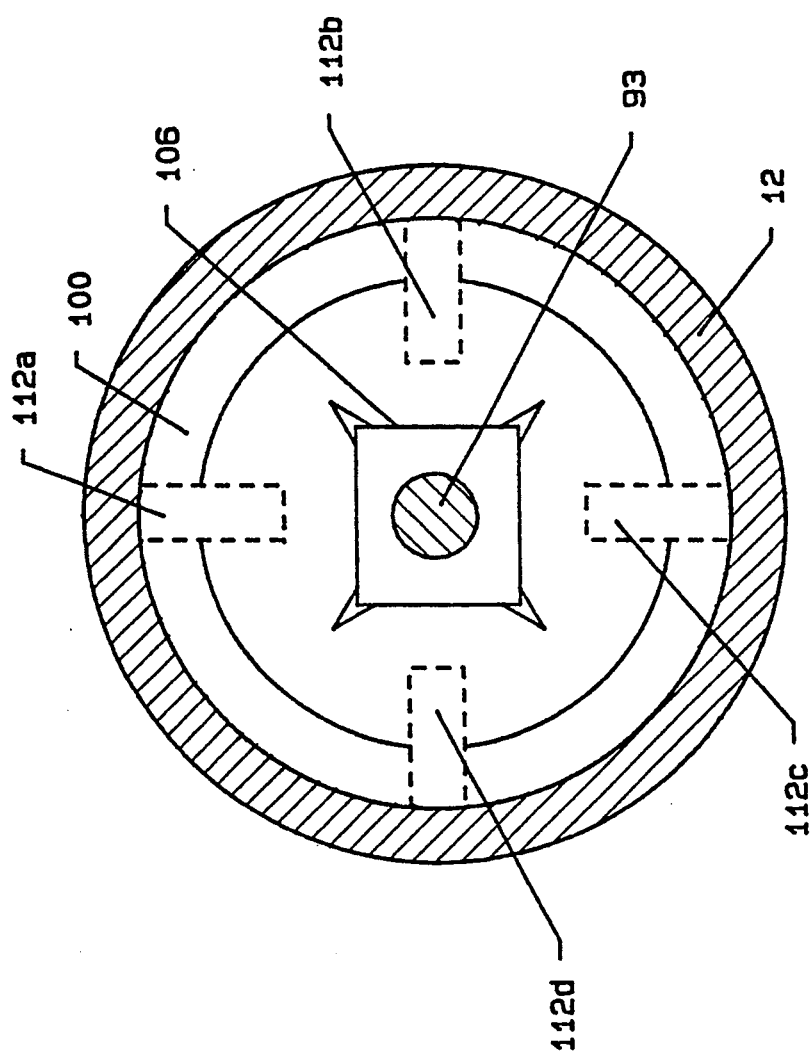
FIG. 9 illustrates a cross-sectional view along line 9—9 of FIG. 10.
Figure 10:
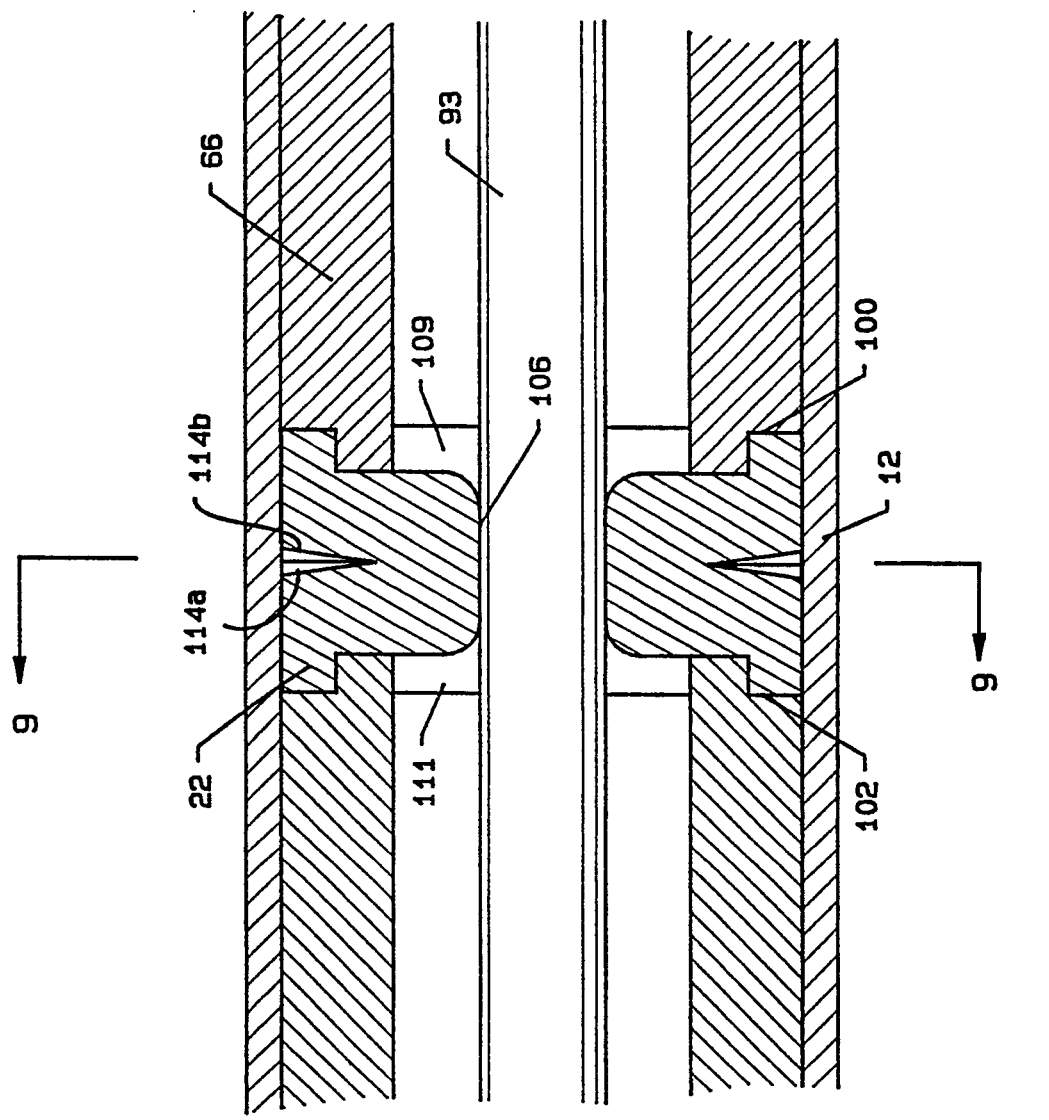
FIG. 10 illustrates the sealing operation of a guidewire or medical device by the compressed compression gasket.

FIGS. 8-10 illustrate the mode of operation where the compression gasket 22 is compressed from each side to seal about the guidewire 93.

FIG. 8 illustrates alignment of the compression gasket in the radiused cavity 50 where all numerals correspond to those elements previously described. Cavities 109 and 111 in the compression gasket 22 are in alignment for accommodation by the annular lips 72 and 51. As the Touhy Borst adapter 14 is advanced on the body 12, the walls of the inner circumference 106 are forced inwardly and downwardly toward the guidewire 93 as illustrated in FIG. 9. The walls of the inner circumference 106 assume rhombic to square to round shape because of influence by the ribs 112a–112d during initial compression and during final compression assume a circular seal about the guidewire 93. As illustrated in FIG. 10, angled walls 114a–114b and corresponding unillustrated angled walls 114c–114d, 114e–114f and 114g–114h fold inwardly towards their like mirror surfaces to aid in full inward movement of the inner circumference to cause sealing of the guidewire 93. A sufficient fluid seal is maintained while still maintaining the ability of the guidewire 93 to slide to and fro in sliding engagement.

Figure 11:
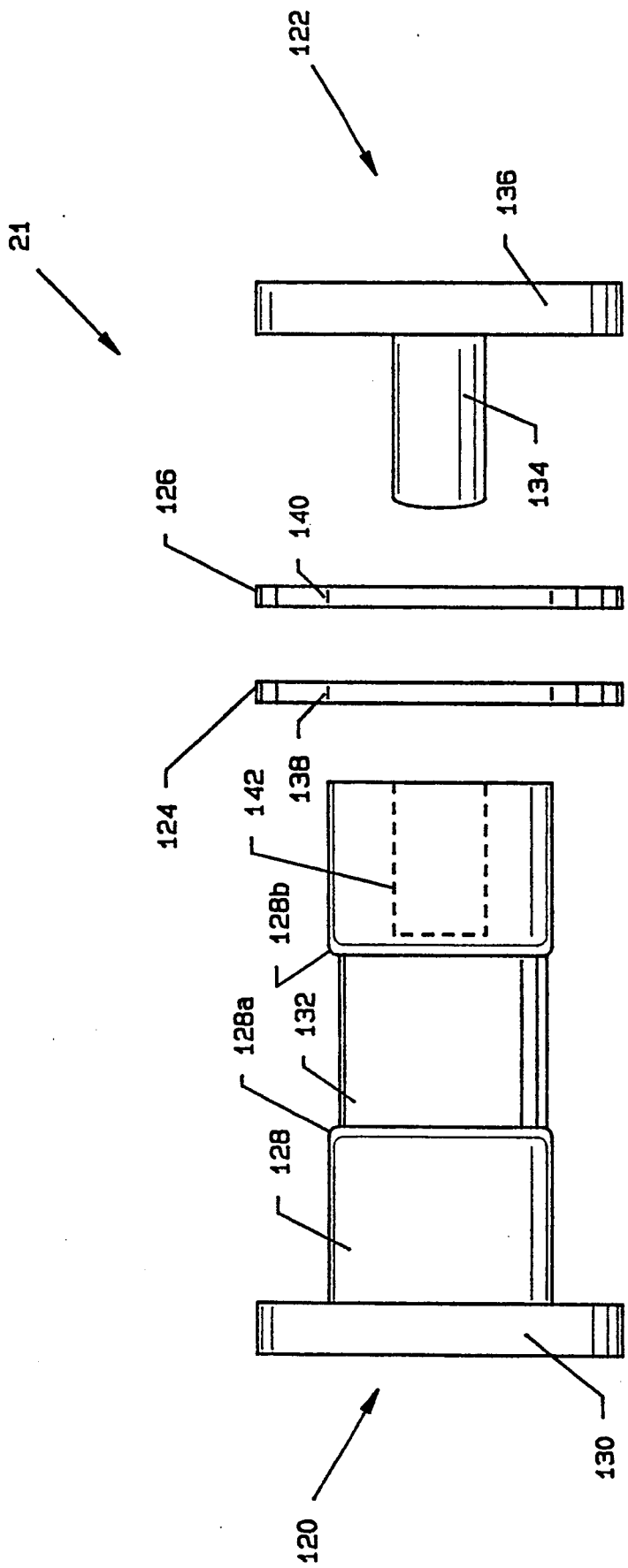
FIG. 11 illustrates an exploded view of the guidewire clamp.
Figure 12:
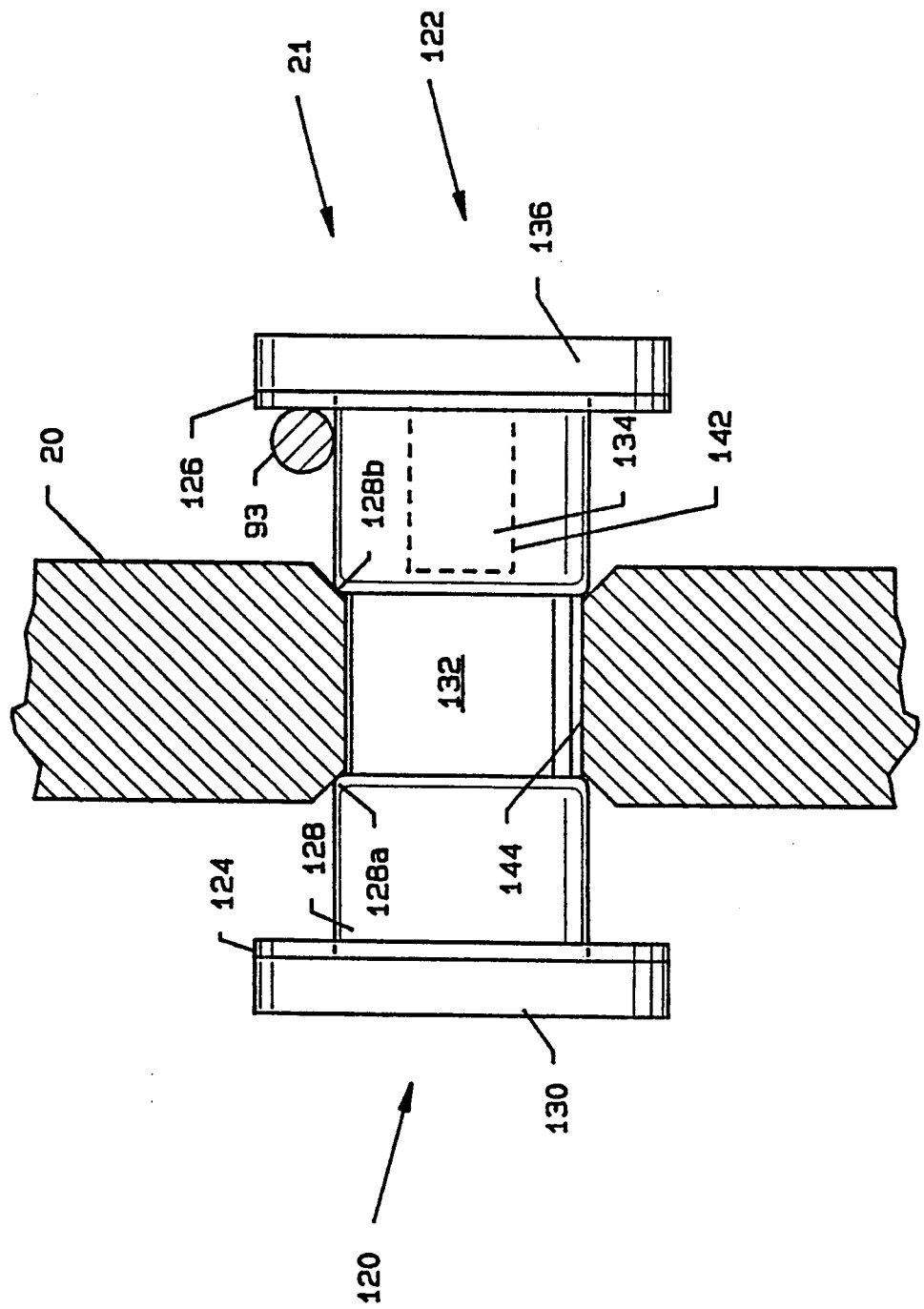
FIG. 12 illustrates the clamp members engaging the side arm.

FIG. 11 illustrates an exploded view of the guidewire clamp 21 which snappingly affixes a guidewire to the side arm support 20 as illustrated in FIG. 1 where all numerals correspond to those elements previously described. The guidewire clamp 21 includes a left clamp member 120, each of which mutually engage each other. Flexible plastic discs 124 and 126 align over and about the left and right clamp members 120 and 122. A multi-radius cylindrical shaft member 128 extends perpendicularly from a disc shaped head 130 and includes a centrally located wide recessed groove 132. Edges 128a and 128b are rounded or can be ramped to transition between the general large radius of the shaft 128 down to the wide groove 132. The right clamp member 122 includes a cylindrical shaft member 134 extending perpendicularly from a disc shaped head 136. The flexible plastic discs 124 and 126 include central holes 138 and 140 for engagement of the flexible plastic discs 124 and 136 over the cylindrical shaft member 128 and 130 as illustrated in FIG. 12. A cylindrical hole 142 in the shaft 128 frictionally engages the cylindrical shaft 134 on the right clamp member shaft 122 to mate the left and right clamp members 120 and 122 through a beveled hole 144 in the side arm 20 as illustrated in FIG. 12.

FIG. 12 illustrates the left and right clamp members engaging the side arm 20 where all numerals correspond to those elements previously described. The flexible plastic discs are cemented to the heads 130 and 136, respectively. The wide groove 132 frictionally and loosely engages the hole 144 to maintain the guidewire clamp 21 in a centrally aligned position with respect to the side arm 20 to allow a guidewire 93 to be readily positioned at either side of the side arm 20 and between either of the flexible plastic discs 124 and 126 and their respective heads.

Figure 13:
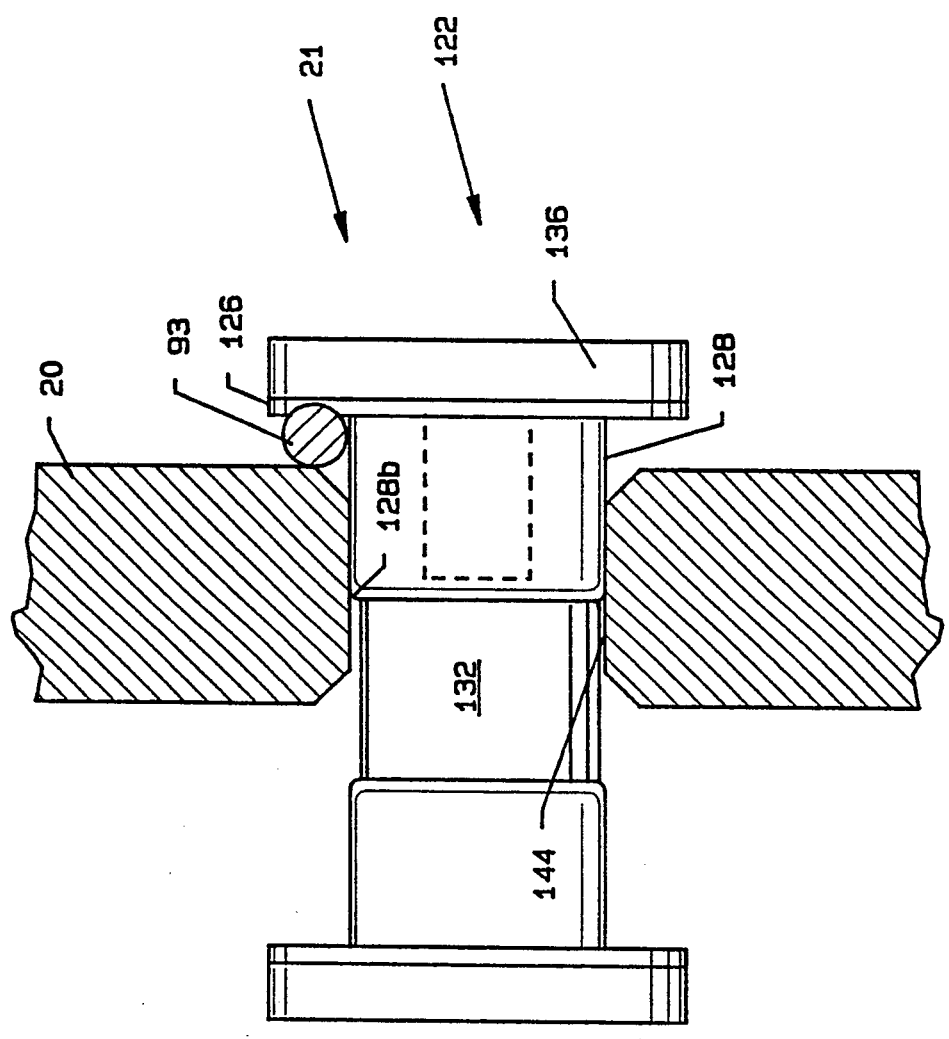
FIG. 13 illustrates a guidewire or medical device frictionally engaged by the guidewire clamp.

FIG. 13 illustrates the mode of operation of the guidewire 93 or medical device frictionally engaged and secured between the side arm 20 and the flexible plastic disc 126 and adjacent disc shaped head 136 where the entire guidewire clamp 21 has been forcibly positioned to the left to effect the securement of the guidewire to the side arm 20. During positioning, the hole 144 disengages from alignment with the wide groove 132 of the shaft 128 by action of the ramp 128b against the beveled edges of the hole 144 to cause the wider radius portion of the cylindrical shaft member 128 to firmly engage the hole 144 for positive securement of the guidewire clamp 21 and guidewire with respect to the side arm 20.

Figure 14:
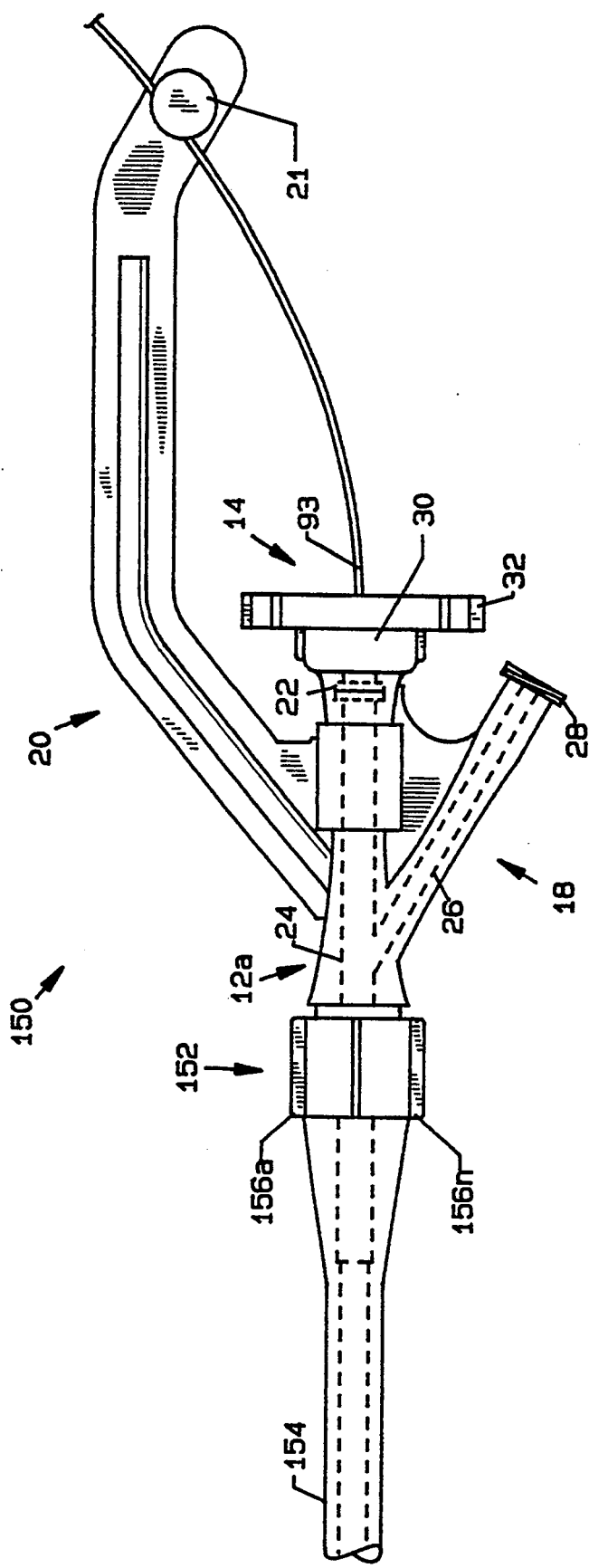
FIG. 14, an alternative embodiment, illustrates a y-connector incorporating a compression seal and a swivel luer and catheter assembly.
Figure 15:
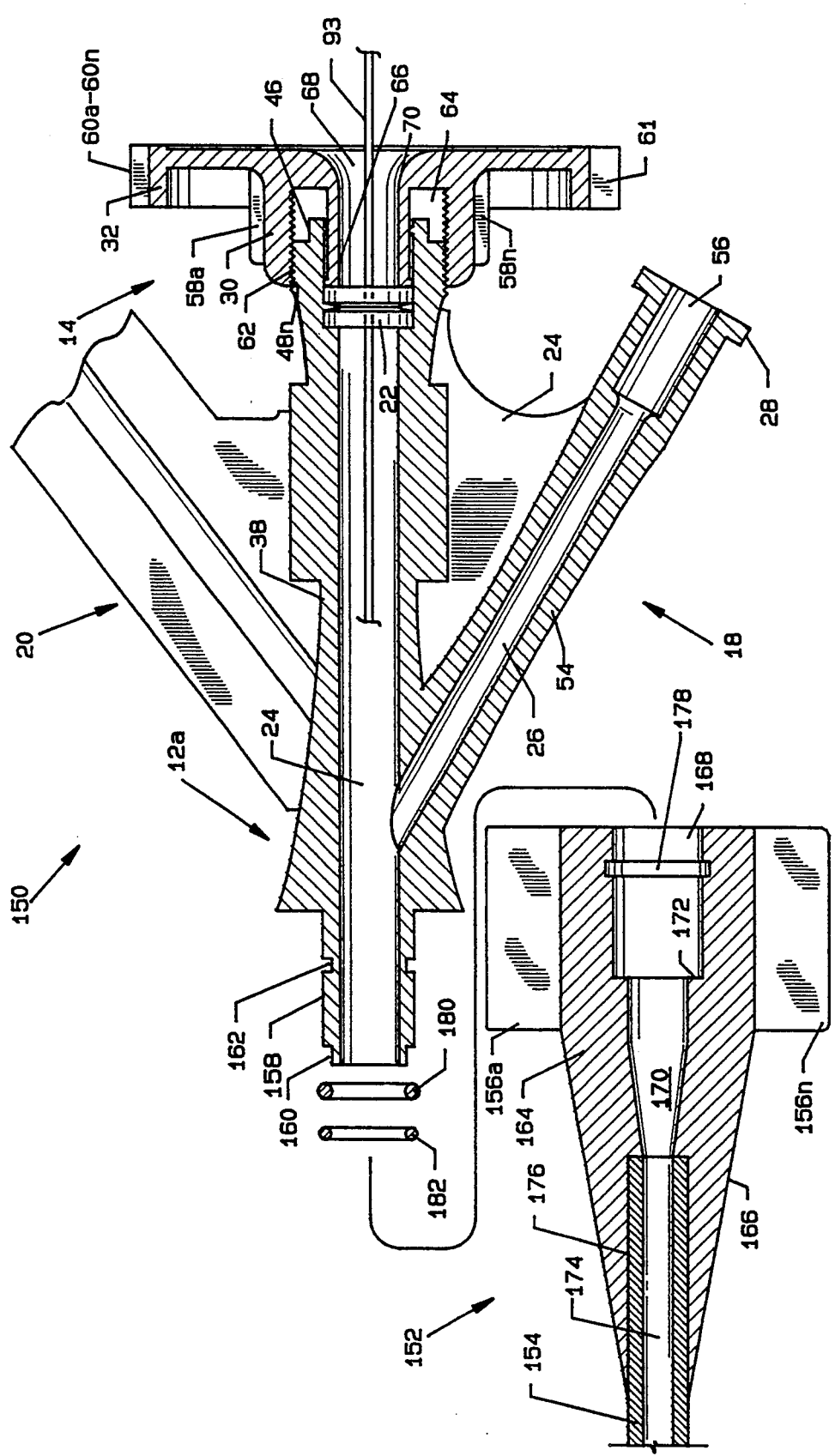
FIG. 15 illustrates a cross-sectional view of the y-connector of FIG. 4.

FIG. 15 illustrates an exploded view in cross section of the rotating y-connector 150 of FIG. 14 where all numerals correspond to those elements previously described. The y-body 12a includes a multi-radius central lumen 24 extending along its axis. The main body 38 includes a cylindrical extension 158 of a lesser radius than that of the main body 38 extending therefrom. An annular ring-like surface 160 is located at one end of the cylindrical extension 158. An annular groove 162 is located about the exterior surface of the cylindrical extension 158.

The swivel luer 152 includes a main swivel luer body 164 which includes a taper 166. A uniform bore 168 and another smaller bore 170, which tapers at one end, align along the axis of the swivel luer body 164. An annular shoulder 172 is located at the inboard end of the uniform bore 168 and between the bores 168 and 170. The guiding catheter shaft 154 includes a central bore 174 and aligns and secures in a bore 176 in the taper 166 of the swivel luer 152. An annular groove 178 is located in the wall of the uniform bore 168. A snap ring 180 and an o-ring 182 are included and described in the following figure.

Figure 16:
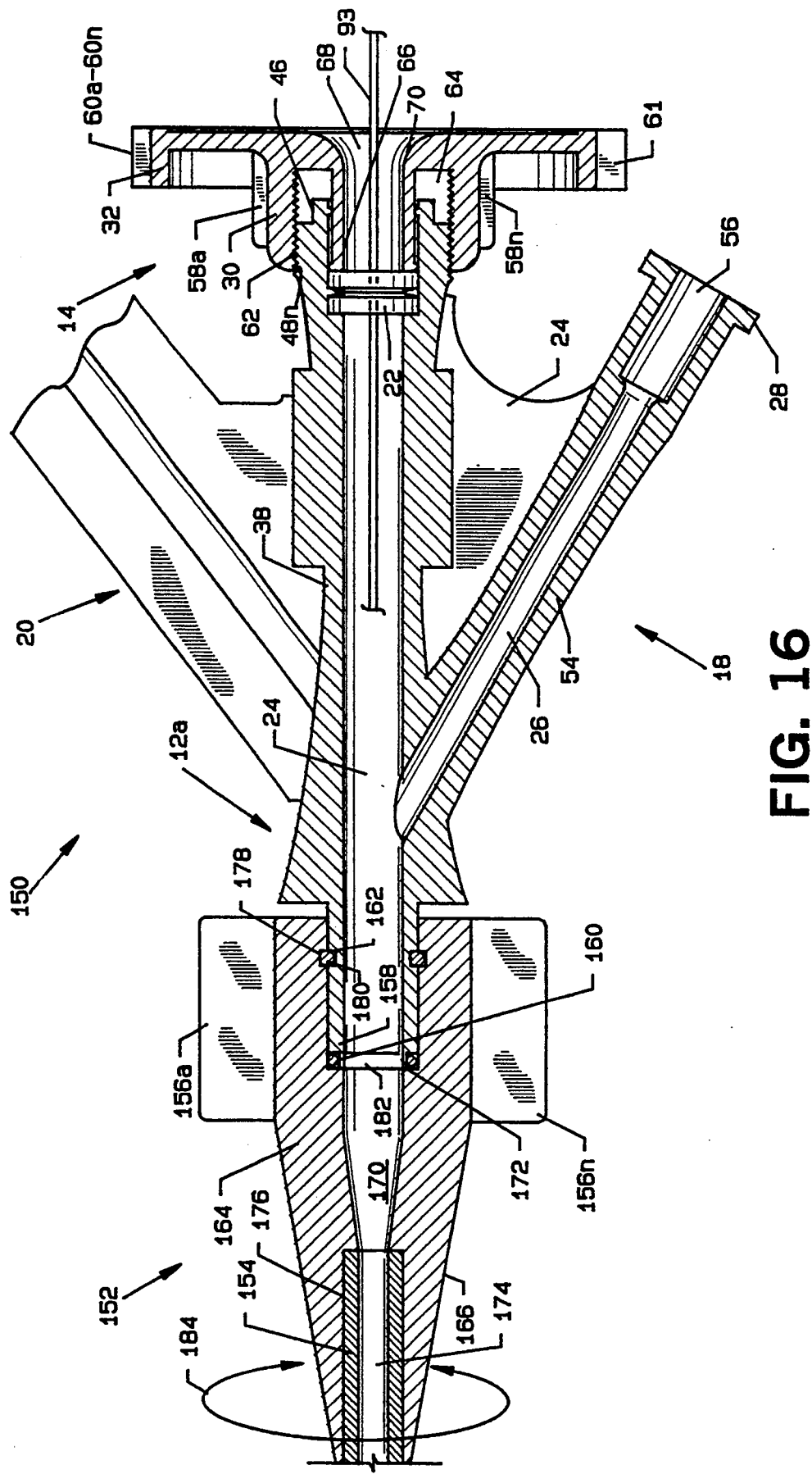
FIG. 16 illustrates a cross-sectional view of the y-connector of FIG. 14.

FIG. 16 illustrates an assembled view of FIG. 15 where all numerals correspond to those elements previously described. The y-body 12a and the swivel luer 152 are joined in a manner allowing a proper seal between the two units while allowing rotation in either rotation of the swivel luer 152 and the guiding catheter shaft 154 about the axis of the rotating y-body 12a, as depicted by rotating arrow 184. The O-ring 182 aligns at one end of the uniform bore 168 against the annular shoulder 172. The annular ring surface 160 and annular shoulder 172 seal against the O-ring 182 to form a sealed union between the lumen 24 of the y-body 12a, and the bore 170 of the swivel luer 152. The snap ring 180 aligns in the annular groove 162 of the cylindrical extension 158 and the annular groove 178 to couple the swivel luer 152 to the y-body 12a. The length of the cylindrical extension 158 is appropriately dimensioned to forcibly contact the O-ring 182, thus insuring a proper seal when the elements are rotated with respect to one another.

FIG. 14, an alternative embodiment, illustrates a side view of a y-connector 150. The y-connector 150 is similar in many aspects to the y-connector 10 and components described in FIGS. 1–13, and the majority of components employed correspond to those elements previously described. A major difference occurs at the distal end where the rotating connector 16 of previously described figures has been replaced by a swivel luer 152 and guiding catheter shaft 154 secured in one end of the swivel luer 152. The distal end of the y-connector body 12 is reconfigured as desired in the following figures to accommodate the swivel luer 152 with the attached catheter shaft 154. The reconfigured body is referred to as a y-connector body 12a where all other illustrated components remain the same as previously described. The swivel luer 152 and the attached guiding catheter shaft rotate about the extended axis of the y-body 12a.

A plurality of finger grip tabs 156a–156n align radially about the exterior of the swivel luer 152 to assist in rotational turning of the swivel luer 152 and the integral guiding catheter shaft 154 with respect to the y-body 12a.

Various modifications can be made to the present invention without departing from the apparent scope hereof.

I claim:

1. In combination, a Y-connector and a compression gasket, comprising:
   a. a Y-connector including a space between an inner rim of a longitudinal lumen and a base of a knurled knob, and means for rotating said Y-connector; and,
   b. a compression gasket in said space and including a geometrically configured cylinder including a top edge, a bottom edge and an inner bore which collapses upon itself when said gasket is in a compressed state and an hour glass configured outer circumference.

2. A Y-connector for medical procedures, comprising:
   a. Y-connector body having a lumen adapted to house a guidewire or catheter; and,
   b. a compression gasket for sealingly compressing said guidewire or catheter, said compression gasket comprising a cylindrical gasket body having a proximal end, a distal end, and a longitudinal inner bore therein; the outer diameters of said proximal end and of said distal end being such as to engage the inner circumferential wall of said Y-connector lumen; said longitudinal inner bore collapsing on itself when said gasket is in a compressed state; said proximal end having a first outer circumferential tapered portion tapering inward towards said inner bore; said distal end having a second outer circumferential tapered portion tapering inward towards said inner bore; said first and said second outer circumferential tapered portions meeting to form in said gasket a portion of outer diameter less than said outer diameters of said proximal end and said distal end; and, said proximal end and said distal end each having an annular cavity formed by a raised annular ring.

3. The Y-connector of claim 2 further comprising a adapter body having a concentric tubular extension with an annular lip configured to engage and accommodate said annular cavity in said compression gasket.

4. The Y-connector of claim 2 wherein said Y-connector body further includes at least one side port.

* * * * *